United States Patent
Zhang et al.

(10) Patent No.: US 6,835,832 B2
(45) Date of Patent: Dec. 28, 2004

(54) PROCESS FOR SYNTHESIS OF HETEROARYL-SUBSTITUTED UREA COMPOUNDS USEFUL AS ANTIINFLAMMATORY AGENTS

(75) Inventors: Lin-Hua Zhang, Foster City, CA (US); Lei Zhu, Milford, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 10/361,731

(22) Filed: Feb. 10, 2003

(65) Prior Publication Data

US 2003/0166931 A1 Sep. 4, 2003

Related U.S. Application Data

(62) Division of application No. 09/611,109, filed on Jul. 6, 2000, now Pat. No. 6,583,282.
(60) Provisional application No. 60/143,094, filed on Jul. 9, 1999.

(51) Int. Cl.$^7$ ................ C07D 295/135; C07D 401/04; C07D 401/14; C07D 403/06; C07D 403/14
(52) U.S. Cl. ............... 544/120; 544/121; 544/122; 544/128; 544/130; 544/131; 544/139; 544/146; 544/153; 544/162
(58) Field of Search ................ 544/120, 121, 544/122, 128, 130, 131, 139, 146, 153, 162

(56) References Cited

U.S. PATENT DOCUMENTS

| | | |
|---|---|---|
| 3,291,808 A | 12/1966 | Elslager et al. |
| 4,105,766 A | 8/1978 | Alexander |
| 4,447,624 A | 5/1984 | Krutak et al. |
| 5,162,360 A | 11/1992 | Creswell et al. |
| 5,686,455 A | 11/1997 | Adams et al. |
| 5,739,143 A | 4/1998 | Adams et al. |
| 5,777,097 A | 7/1998 | Lee et al. |
| 5,783,664 A | 7/1998 | Lee et al. |
| 5,859,041 A | 1/1999 | Liverton et al. |
| 5,869,043 A | 2/1999 | McDonnell et al. |
| 5,871,934 A | 2/1999 | Lee et al. |
| 5,916,760 A | 6/1999 | Goeddel et al. |
| 5,948,885 A | 9/1999 | Stein et al. |
| 6,242,453 B1 | 6/2001 | Cirillo et al. |
| 6,297,381 B1 | 10/2001 | Cirillo et al. |
| 6,358,945 B1 | 3/2002 | Breitfelder et al. |

FOREIGN PATENT DOCUMENTS

| | | |
|---|---|---|
| DD | 293 352 | 8/1991 |
| EP | 61228444 | 10/1986 |
| EP | 0 272 866 | 6/1988 |
| EP | 0692483 | 1/1996 |
| EP | 0859054 | 8/1998 |
| EP | 0922762 | 6/1999 |
| WO | WO 94/22866 | 10/1994 |
| WO | WO 96/25157 | 8/1996 |
| WO | WO 96/40143 | 12/1996 |
| WO | WO 97/22704 | 6/1997 |
| WO | WO 97/33883 | 9/1997 |
| WO | WO 97/35855 | 10/1997 |
| WO | WO 97/35856 | 10/1997 |
| WO | WO 97/44467 | 11/1997 |
| WO | WO 97/47618 | 12/1997 |
| WO | WO 97/48697 | 12/1997 |
| WO | WO 98/07425 | 2/1998 |
| WO | WO 98/15618 | 4/1998 |
| WO | WO 98/27098 | 6/1998 |
| WO | WO 98/52558 | 11/1998 |
| WO | WO 98/52559 | 11/1998 |
| WO | WO 99/00357 | 1/1999 |
| WO | WO 99/32106 | 7/1999 |
| WO | WO 99/32110 | 7/1999 |
| WO | WO 99/32111 | 7/1999 |
| WO | WO 99/32455 | 7/1999 |
| WO | WO 99/32463 | 7/1999 |
| WO | WO 99/46244 | 9/1999 |
| WO | WO 00/43384 | 7/2000 |

OTHER PUBLICATIONS

Jeffrey C. Boehm & Jerry L. Adams, New inhibitors of p38 kinase, Expert Opin.Ther. Patents (2000) 10(1):25–37.
Two novel structural classes of P38 kinase inhibitors; Exp. Opin. Ther. Patents (1999) 9(4) 477–480.
SB 203580, Calbiochem—Cat. No. 559389—Revised May 30, 1997.
Jagadish C. Sircar, et al; Pyrazolo[5,1-b]quinazolin-9 ones: A New Series of Antiallergic Agents, J. Med. Chem. 1981, 24, 735–742.

*Primary Examiner*—Mark L. Berch
*Assistant Examiner*—Kahsay Habte
(74) *Attorney, Agent, or Firm*—Robert P. Raymond; Anthony P. Bottino; Timothy X. Witkowski

(57) ABSTRACT

Disclosed are novel processes and novel intermediate compounds for preparing aryl-and heteroaryl-substituted urea compounds of the formula(I) wherein $Ar_1$, $Ar_2$, L, Q and X are described herein. The product compounds are useful in pharmaceutic compositions for treating diseases or pathological conditions involving inflammation such as chronic inflammatory diseases.

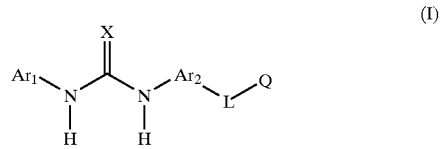

(I)

7 Claims, No Drawings

PROCESS FOR SYNTHESIS OF HETEROARYL-SUBSTITUTED UREA COMPOUNDS USEFUL AS ANTIINFLAMMATORY AGENTS

RELATED APPLICATION DATA

This application is a divisional application of U.S. application Ser. No. 09/611,109 filed Jul. 6, 2000 now U.S. Pat. No. 6,583,282, which claims benefit of Ser. No. 60/143,094 filed Jul. 9, 1999.

TECHNICAL FIELD OF THE INVENTION

This invention relates to novel processes for preparing new aryl-and heteroaryl-substituted urea compounds of formula (I):

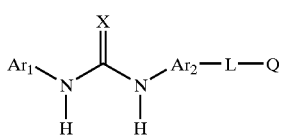

(I)

wherein $Ar_1$, $Ar_2$, X, L and Q are defined below, which are useful for treating diseases and pathological conditions involving inflammation such as chronic inflammatory disease.

BACKGROUND OF THE INVENTION

Aryl- and heteroaryl-substituted ureas have been described as inhibitors of cytokine production. Examples of such compounds are reported in WO 99/23091 and in WO 98/52558. These inhibitors are described as effective therapeutics in cytokine-mediated diseases, including inflammatory and autoimmune diseases.

A key step in the synthesis of these compounds is the formation of the urea bond. Various methods have been reported to accomplish this. For example, as reported in the above references, an aromatic or heteroaromatic amine, II, may be reacted with an aromatic or heteroaromatic isocyanate III to generate the urea IV (Scheme I)

Scheme I

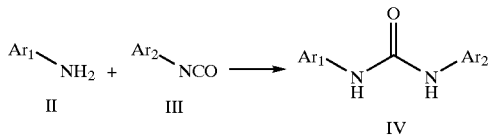

If not commercially available, one may prepare the isocyanate III by reaction of an aryl or heteroaryl amine $Ar_2NH_2$ with phosgene or a phosgene equivalent, such as bis(trichloromethyl) carbonate (triphosgene) (P. Majer and R. S. Randad, J. Org. Chem. 1994, 59, 1937) or trichloromethyl chloroformate (diphosgene). K. Kurita, T. Matsumura and Y. Iwakura, J. Org. Chem. 1976, 41, 2070) to form the isocyanate III, followed by reaction with $Ar_1NH_2$ to provide the urea. Other approaches to forming the urea known in the chemical literature are to form a carbamate, as shown in Scheme II below, by reaction of an amine with a chloroformate derivative, such as phenyl chloroformate (B. Thavonekham, Synthesis, 1997, 1189), chloromethyl chloroformate (T. Patonay, E. Patonay-Peli, L Zolnai and F. Mogyorodi, Synthetic Communications, 1996, 26, 4253), p-nitrophenyl chloroformate (J. Gante, Chem. Ber. 1965, 98, 3334), or 2,4,5-trichlorophenyl chloroformate (A. W. Lipkowski, S. W. Tam and P. S. Portoghese, J. Med. Chem. 1986, 29, 1222) to form a carbamate V. This may then be reacted with an aryl or heteroaryl amine (II) to provide urea IV (Scheme II—reaction with phenyl chloroformate shown). The synthesis of ureas through (phenoxycarbonyl)tetrazole (R. W. Adamiak, J. Stawinski, Tetrahedron Lett. 1977, 1935) or 1,1'-carbonylbisbenzotriazole (A. R. Katritzky, D. P. M. Pleynet and B. Yang, J. Org. Chem. 1997, 62, 4155) has been reported. In addition, preparation of ureas by catalytic carbonation of amines with carbon monoxide or carbon dioxide has been documented in the literature (N. Sonoda, T. Yasuhara, K. Kondo, T. Ikeda and S. Tsutsumi, J. Am. Chem. Soc. 1971, 93, 691; Y. Morimoto, Y. Fujiwara, H. Taniguchi, Y. Hori and Y. Nagano, Tetrahedron Lett. 1986, 27, 1809). In each of these cases, $Ar_1$ and $Ar_2$ may be modified before and/or after the urea formation to produce desired compounds.

Scheme II

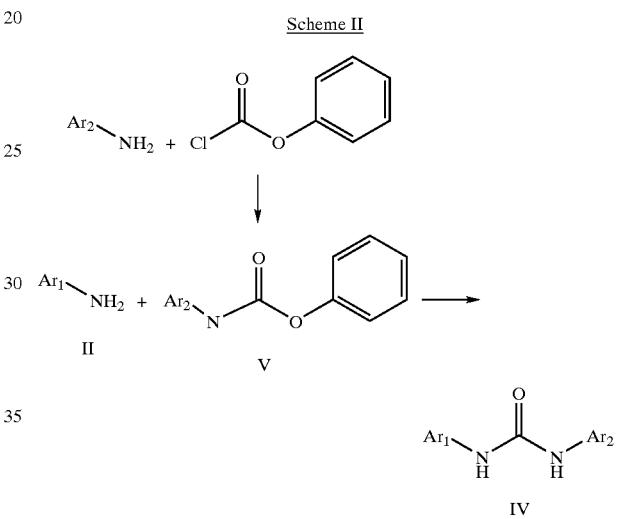

Each of the methods described above suffer from one or more disadvantages. For example, phosgene and phosgene equivalents are hazardous and dangerous to use, particularly in large-scale applications. In addition the isocyanate intermediate III is not stable and may undergo decomposition during preparation and storage. The urea formation may be done using a phenyl carbamate, as illustrated in Scheme II and U.S. application Ser. No. 09/484,638. However, the by-product phenol formed in the urea synthesis does not have sufficient water solubility to be easily removed by water washing especially at large scale. Thus it may require multiple washing and several crystallizations to obtain highly pure product. For these reasons these methods are not well-suited for industrial-scale production.

U.S. application Ser. No. 09/484,638 also discloses the synthesis of substituted naphthyl amino intermediates for use in making aryl-and heteroaryl-substituted urea compounds of the formula(I) as described therein. This synthesis begins with 4-aminonapthol which is protected with a Boc (tert-butoxycarbonyl) group on the amine prior to alkylation and deprotection. This procedure is also not amenable to industrial-scale production. The starting 4-aminonaphthol is very expensive and not available in large quantity. In addition the protection and deprotection steps are tedious and add to the expense.

Disclosed herein are novel processes for making the aryl-and heteroaryl-substituted urea compounds of the formula(I)

including those disclosed in U.S. application Ser. No. 09/484,638 and novel intermediates useful in such processes.

BRIEF SUMMARY OF THE INVENTION

It is therefore an object of this invention to provide a general and cost-effective process for the preparation of the aryl- and heteroaryl-substituted urea compounds of the formula(I) shown below:

$$Ar_1\underset{H}{\overset{X}{\underset{N}{\|}}}\underset{H}{\overset{}{\underset{N}{\|}}}Ar_2-L-Q \quad (I)$$

comprising the steps of:

reacting of intermediate of formula (II) with intermediate of formula (IV) to produce the product compound of formula (I):

$$Ar_1\underset{H}{\overset{X}{\underset{N}{\|}}}ORa \;+\; H_2N\underset{L}{\overset{Ar_2}{\diagup}}Q \longrightarrow$$

(II)                    (IV)

$$Ar_1\underset{H}{\overset{X}{\underset{N}{\|}}}\underset{H}{\overset{}{\underset{N}{\|}}}Ar_2-L-Q$$

(I)

wherein $Ar_1$, $Ar_2$, L, Q, X and Ra are as described below.

In addition, this invention provides efficient methods for preparing intermediates used in the preparation of preferred cytokine-inhibiting aryl-and heteroaryl-substituted ureas. These processes are especially well-suited for preparation of these compounds on an industrial scale.

DETAILED DESCRIPTION OF THE INVENTION

The present invention is directed to the synthesis of compounds having formula (I):

$$Ar_1\underset{H}{\overset{X}{\underset{N}{\|}}}\underset{H}{\overset{}{\underset{N}{\|}}}Ar_2-L-Q \quad (I)$$

wherein:

$Ar_1$ is a heterocyclic group selected from the group consisting of phenyl, pyridine, pyridone, pyrrole, pyrrolidine, pyrazole, imidazole, oxazole, thiazole, furan and thiophene; wherein $Ar_1$ is optionally substituted by one or more $R_1$, $R_2$ or $R_3$;

$Ar_2$ is:

phenyl, naphthyl, quinoline, isoquinoline, tetrahydronaphthyl, tetrahydroquinoline, tetrahydroisoquinoline, benzimidazole, benzofuran, indanyl, indenyl or indole each being optionally substituted with one to three $R_2$ groups;

L, a linking group, is:
$C_{1-10}$ saturated or unsaturated branched or unbranched carbon chain;
wherein one or more methylene groups are optionally independently replaced by O,N or S; and
wherein said linking group is optionally substituted with 0–2 oxo groups and one or more $C_{1-4}$ branched or unbranched alkyl optionally substituted by one or more halogen atoms;
or L is a cyclic group which is:
a) a $C_{5-8}$ cycloalkyl or cycloalkenyl optionally substituted with 1–2 oxo groups, 1–3 $C_{1-4}$ branched or unbranched alkyl, $C_{1-4}$ alkoxy or $C_{1-4}$ alkylamino chains;
b) phenyl, furan, thiophene, pyrrole, imidazolyl, pyridine, pyrimidine, pyridinone, dihydropyridinone, maleimide, dihydromaleimide, piperdine, piperazine or pyrazine each being optionally independently substituted with 1–3 $C_{1-4}$ branched or unbranched alkyl, $C_{1-4}$alkoxy, hydroxy, cyano, mono- or di-($C_{1-3}$ alkyl)amino, $C_{1-6}$ alkyl-S(O)$_q$, or halogen;
wherein said cyclic group is optionally attached to a $C_{1-4}$ saturated or unsaturated branched or unbranched carbon chain wherein said carbon chain is in turn covalently attached to Q, said carbon chain is optionally partially or fully halogenated and wherein one or more methylene groups are optionally replaced by O, NH, S(O), S(O)$_2$ or S, wherein said methylene groups are further optionally independently substituted with 1–2 oxo groups and one or more $C_{1-4}$ branched or unbranched alkyl optionally substituted by one or more halogen atoms;

Q is selected from the group consisting of:
a) phenyl, naphthyl, pyridine, pyrimidine, pyridazine, imidazole, benzimidazole, furan, thiophene, pyran, naphthyridine, oxazo[4,5-b]pyridine and imidazo[4,5-b]pyridine, which are optionally substituted with one to three groups selected from the group consisting of halogen, $C_{1-6}$ alkyl, $C_{1-6}$ alkoxy, hydroxy, mono- or di-($C_{1-3}$ alkyl)amino, $C_{1-6}$ alkyl-S(O)$_m$ and phenylamino wherein the phenyl ring is optionally substituted with one to two groups selected from the group consisting of halogen, $C_{1-6}$ alkyl and $C_{1-6}$ alkoxy;
b) tetrahydropyran, tetrahydrofuran, 1,3-dioxolanone, 1,3-dioxanone, 1,4-dioxane, morpholine, thiomorpholine, thiomorpholine sulfoxide, thiomorpholine sulfone, piperidine, piperidinone, tetrahydropyrimidone, cyclohexanone, cyclohexanol, pentamethylene sulfide, pentamethylene sulfoxide, pentamethylene sulfone, tetramethylene sulfide, tetramethylene sulfoxide and tetramethylene sulfone which are optionally substituted with one to three groups selected from the group consisting of $C_{1-6}$ alkyl, $C_{1-6}$ alkoxy, hydroxy, mono- or di-($C_{1-3}$ alkyl) amino-$C_{1-3}$ alkyl, phenylamino-$C_{1-3}$ alkyl and $C_{1-3}$ alkoxy-$C_{1-3}$ alkyl;
c) $C_{1-6}$ alkoxy, secondary or tertiary amine wherein the amino nitrogen is covalently bonded to groups selected from the group consisting of $C_{1-3}$ alkyl and $C_{1-5}$ alkoxyalkyl and phenyl wherein the phenyl ring is optionally substituted with one to two groups selected from the group consisting of halogen, $C_{1-6}$ alkoxy, hydroxy or mono- or di-($C_{1-3}$ alkyl)amino, $C_{1-6}$ alkyl-S(O)$_r$ and phenyl-S(O)$_r$, wherein the phenyl ring is optionally substituted with one to two groups consisting of halogen, $C_{1-6}$ alkoxy, hydroxy and mono- or di-($C_{1-3}$ alkyl)amino;

$R_1$ is selected from the group consisting of:
(a) $C_{3-10}$ branched or unbranched alkyl, which may optionally be partially or fully halogenated, and optionally substituted with one to three phenyl, naphthyl or heterocyclic groups selected from the group consisting of pyridinyl, pyrimidinyl, pyrazinyl, pyridazinyl, pyrrolyl, imidazolyl, pyrazolyl, thienyl, furyl, isoxazolyl and isothiazolyl; each such phenyl, naphthyl or heterocycle selected from the group hereinabove described, being substituted with 0 to 5 groups selected from the group consisting of halogen, $C_{1-6}$ branched or unbranched alkyl which is optionally partially or fully halogenated, $C_{3-8}$ cycloalkyl, $C_{5-8}$ cycloalkenyl, hydroxy, cyano, $C_{1-3}$ alkyloxy which is optionally partially or fully halogenated, $NH_2C(O)$ and di($C_{1-3}$)alkylaminocarbonyl;

(b) $C_{3-7}$ cycloalkyl selected from the group consisting of cyclopropyl, cyclobutyl, cyclopentanyl, cyclohexanyl, cycloheptanyl, bicyclopentanyl, bicyclohexanyl and bicycloheptanyl, which are optionally partially or fully halogenated and optionally substituted with one to three $C_{1-3}$ alkyl groups, or an analog of such cycloalkyl group wherein one to three ring methylene groups are replaced by groups independently selected from O, S, CHOH, >C=O, >C=S and NH;

(c) $C_{3-10}$ branched alkenyl optionally partially or fully halogenated, and optionally substituted with one to three $C_{1-5}$ branched or unbranched alkyl, phenyl, naphthyl or heterocyclic groups, with each such heterocyclic group being independently selected from the group consisting of pyridinyl, pyrimidinyl, pyrazinyl, pyridazinyl, pyrrolyl, imidazolyl, pyrazolyl, thienyl, furyl, isoxazolyl and isothiazolyl, and each such phenyl, naphthyl or heterocyclic group being substituted with 0 to 5 groups selected from halogen, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, hydroxy, cyano, $C_{1-3}$ alkyloxy which is optionally partially or fully halogenated, $NH_2C(O)$ and mono- or di($C_{1-3}$)alkylaminocarbonyl;

(d) $C_{5-7}$ cycloalkenyl selected from the group consisting of cyclopentenyl, cyclohexenyl, cyclohexadienyl, cycloheptenyl, cycloheptadienyl, bicyclohexenyl and bicycloheptenyl, wherein such cycloalkenyl group is optionally substituted with one to three $C_{1-3}$ alkyl groups;

(e) cyano; and, (f) methoxycarbonyl, ethoxycarbonyl and propoxycarbonyl;

$R_2$ is selected from the group consisting of:

a $C_{1-6}$ branched or unbranched alkyl optionally partially or fully halogenated, acetyl, aroyl, $C_{1-4}$ branched or unbranched alkoxy optionally partially or fully halogenated, halogen, methoxycarbonyl and phenylsulfonyl;

$R_3$ is selected from the group consisting of:

a) a phenyl, naphthyl or heterocyclic group selected from the group consisting of pyridinyl, pyrimidinyl, pyrazinyl, pyridazinyl, pyrrolyl, imidazolyl, pyrazolyl, thienyl, furyl, tetrahydrofuryl, isoxazolyl, isothiazolyl, quinolinyl, isoquinolinyl, indolyl, benzimidazolyl, benzofuranyl, benzoxazolyl, benzisoxazolyl, benzpyrazolyl, benzothiofuranyl, cinnolinyl, pterindinyl, phthalazinyl, naphthypyridinyl, quinoxalinyl, quinazolinyl, purinyl and indazolyl wherein such phenyl, naphthyl or heterocyclic group is optionally substituted with one to five groups selected from the group consisting of a $C_{1-6}$ branched or unbranched alkyl, phenyl, naphthyl, heterocycle selected from the group hereinabove described, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halo, hydroxy, cyano, $C_{1-3}$ alkyloxy which may optionally be partially or fully halogenated, phenyloxy, naphthyloxy, heteraryloxy wherein the heterocyclic moiety is selected from the group hereinabove described, nitro, amino, mono- or di-($C_{1-3}$)alkylamino, phenylamino, naphthylamino, heterocyclylamino wherein the heterocyclyl moiety is selected from the group hereinabove described, $NH_2C(O)$, a mono- or di-($C_{1-3}$)alkyl aminocarbonyl, $C_{1-5}$ alkyl-C(O)—$C_{1-4}$ alkyl, amino-$C_{1-5}$ alkyl, mono- or di-($C_{1-3}$)alkylamino-$C_{1-5}$ alkyl, amino-S(O)$_2$, di-($C_{1-3}$)alkylamino-S(O)$_2$, $R_4$—$C_{1-5}$ alkyl, $R_5$—$C_{1-5}$ alkoxy, $R_6$—C(O)—$C_{1-5}$ alkyl and $R_7$—$C_{1-5}$ alkyl-N($R_8$)—;

b) a fused aryl selected from the group consisting of benzocyclobutanyl, indanyl, indenyl, dihydronaphthyl, tetrahydronaphthyl, benzocycloheptanyl and benzocycloheptenyl, or a fused heterocyclyl selected from cyclopentenopyridine, cyclohexanopyridine, cyclopentanopyrimidine, cyclohexanopyrimidine, cyclopentanopyrazine, cyclohexanopyrazine, cyclopentanopyridazine, cyclohexanopyridazine, cyclopentanoquinoline, cyclohexanoquinoline, cyclopentanoisoquinoline, cyclohexanoisoquinoline, cyclopentanoindole, cyclohexanoindole, cyclopentanobenzimidazole, cyclohexanobenzimidazole, cyclopentanobenzoxazole, cyclohexanobenzoxazole, cyclopentanoimidazole, cyclohexanoimidazole, cyclopentanothiophene and cyclohexanothiophene; wherein the fused aryl or fused heterocyclyl ring is substituted with 0 to 3 groups independently selected from phenyl, naphthyl, heterocyclyl selected from the group consisting of pyridinyl, pyrimidinyl, pyrazinyl, pyridazinyl, pyrrolyl, imidazolyl, pyrazolyl, thienyl, furyl, isoxazolyl, and isothiazolyl, $C_{1-6}$ branched or unbranched alkyl which is optionally partially or fully halogenated, halo, cyano, $C_{1-3}$ alkyloxy which is optionally partially or fully halogenated, phenyloxy, naphthyloxy, heterocyclyloxy wherein the heterocyclyl moiety is selected from the group hereinabove described, nitro, amino, mono- or di-($C_{1-3}$)alkylamino, phenylamino, naphthylamino, heterocyclylamino wherein the heterocyclyl moiety is selected from the group hereinabove described, $NH_2C(O)$, a mono- or di-($C_{1-3}$)alkyl aminocarbonyl, $C_{1-4}$ alkyl-OC(O), $C_{1-5}$ alkyl-C(O)—$C_{1-4}$ branched or unbranched alkyl, an amino-$C_{1-5}$ alkyl, mono- or di-($C_{1-3}$)alkylamino-$C_{1-5}$ alkyl, $R_9$—$C_{1-5}$ alkyl, $R_{10}$—$C_{1-5}$ alkoxy, $R_{11}$—C(O)—$C_{1-5}$ alkyl and $R_{12}$—$C_{1-5}$ alkyl-N($R_{13}$)—;

c) cycloalkyl selected from the group consisting of cyclopentanyl, cyclohexanyl, cycloheptanyl, bicyclopentanyl, bicyclohexanyl and bicycloheptanyl, wherein the cycloalkyl is optionally partially or fully halogenated and optionally substituted with one to three $C_{1-3}$ alkyl groups;

d) $C_{5-7}$ cycloalkenyl, selected from the group consisting of cyclopentenyl, cyclohexenyl, cyclohexadienyl, cycloheptenyl, cycloheptadienyl, bicyclohexenyl and bicycloheptenyl, wherein such cycloalkenyl group is optionally substituted with one to three $C_{1-3}$ alkyl groups;

e) acetyl, aroyl, alkoxycarbonylalkyl and phenylsulfonyl; and f) $C_{1-6}$ branched or unbranched alkyl optionally partially or fully halogenated;

$R_1$ and $R_2$ taken together optionally form a fused phenyl or pyridinyl ring;

each $R_8$ or $R_{13}$ is independently selected from the group consisting of:

hydrogen and $C_{1-4}$ branched or unbranched alkyl optionally partially or fully halogenated;

each $R_4$, $R_5$, $R_6$, $R_7$, $R_9$, $R_{10}$, $R_{11}$ and $R_{12}$ is independently selected from the group consisting of:

morpholine, piperidine, piperazine, imidazole and tetrazole;

m is 0, 1 or 2;

q is 0, 1 or 2;

r is 0, 1 or 2;

t is 0, 1 or 2; and

X is O or S.

The compounds of the invention may be prepared as physiologically and pharmaceutically acceptable salts, as may seem appropriate to one of ordinary skill in the art.

The compounds produced by the novel process of the invention are only those which are contemplated to be 'chemically stable' as will be appreciated by those skilled in the art. For example, a compound which would have a 'dangling valency', or a 'carbanion' are not compounds contemplated to be made by the novel process.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, pentoxy and hexoxy. All alkyl, alkenyl and alkynyl groups shall be understood as being branched or unbranched where structurally possible and unless otherwise specified. Other more specific definitions are as follows:

The term "aroyl" as used in the present specification shall be understood to mean "benzoyl" or "naphthoyl".

NMP: 1-methyl-2-pyrrolidinone;
THF: tetrahydrofuran;
DMF: N,N'-dimethylformamide;
DMAC: N-N'-dimethylacetamide;
DMSO: dimethylsulfoxide;
DMAP: 4-dimethylaminopyridine;
DBU: 1,8-diazabicyclo[5.4.0]undec-7-ene;

PROCESS FOR MAKING COMPOUNDS OF THE FORMULA(I)

The novel process comprises:

Step 1

Reacting in a suitable solvent an amino-heterocycle $NH_2$—$Ar_1$ with a haloformate RaOC(X)Ha, wherein Ra represents $C_{2-3}$ halocarbon, preferably 2,2,2-trichloroethyl, and Ha represents halogen, preferably chloro, X is as defined above, in the presence of a suitable base, to produce carbamate of the formula (II):

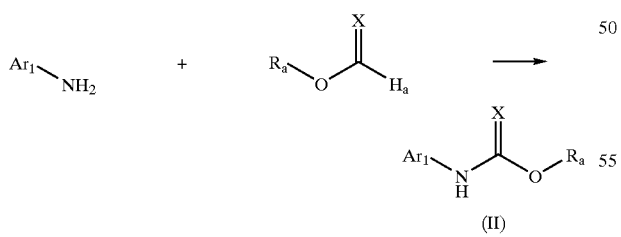

(II)

Preferable formate RaOC(X)Ha are those, which upon hydrolysis of the formula(II) intermediates, will form a water soluble byproduct which is easily removed by aqueous washing, such byproduct would be, for example, 2,2,2-trichloroethanol. Examples of preferred RaOCOHa are trichloroethyl chloroformate or trichloroethyl chlorothioformate. Accordingly, a preferred compound of the formula(II) is:

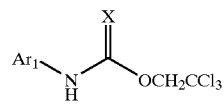

Synthesis of amino-heterocycle $NH_2$—$Ar_1$ has been illustrated in U.S. patent application Ser. No. 09/484,638, incorporated herein by reference. A particularly preferred compound of the formula(II) is where $Ar_1$ is 1-tolyl-3-t-butyl-pyrazole-5-yl.

Reaction conditions such as the selection of a suitable solvent and temperature is within the skill of the ordinary artisan depending on the particular compounds desired. Typically, the reaction of step 1 is in a non-aqueous or an aqueous solvent, preferably THF or ethyl acetate, in the presence of a suitable base such as tertiary amine for example triethylamine, diisopropylethylamine, N-methylpyrrolidine, DBU(1,8-diazabicyclo[5.4.0]undec-7-ene), DMAP(4-dimethylaminopyridine), N-methylmorpholine, pyridine, methyl pyridine or inorganic bases such as sodium hydroxide, sodium carbonate, sodium bicarbonate, potassium hydroxide, potassium carbonate and potassium bicarbonate. Preferred suitable bases for step 1 are diisopropylethylamine, NaOH or N-methylpyrrolidine. The reaction occurs at a temperature of about 0–100° C., preferably 5–15° C., for about 0.5–24 hrs, preferably 3–4 hrs.

Step 2

For certain preferred embodiments, Step 2 proceeds as follows. Reacting a Z—$Ar_2$—MH, where Z is a nitro or nitroso group, M is O, S, or NH, and $Ar_2$ is as defined hereinabove, with a Y-J-Q moiety in a suitable solvent to produce the intermediate of formula (III)

(III)

wherein L and Q are as defined hereinabove, Y is a leaving group such as a halogen and M-J constitutes L;

A suitable solvent for the above reaction would be a polar non-protic organic solvent, such as acetonitrile, DMF (N,N'-dimethylformamide), DMAC (N-N'-dimethylacetamide), DMSO (dimethylsulfoxide) and NMP (1-methyl-2-pyrrolidinone), preferably NMP, at a temperature of about 50–100° C., preferably between 75–95° C., for about 0.5–24 hrs, preferably 3–4 hrs.

For other embodiments of L, analogous methods can be found in U.S. patent application Ser. Nos. 09/484,638 and 09/505,582 incorporated in their entirety by reference.

Step 3

Reducing compound of formula (III) with catalytic hydrogenation or non-catalytic reduction to produce the intermediate of formula (IV):

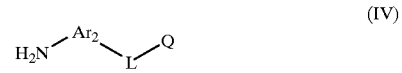

(IV)

Catalytic hydrogenation is preferred, a preferred catalyst is Pd/C. Reaction conditions such as the selection of a suitable solvent and temperature is within the skill of the ordinary artisan. The catalytic hydrogenation with respect to $H_2$ pressure and time can be varied, a preferable hydrogenation occurs under about 30 psi for about 1 hr–24 hours.

Step 4

Reacting the intermediate of formula (II) with the intermediate of formula (IV) with or without base, preferably with a base. A suitable base will be one such as tertiary amine for example triethylamine, diisopropylethylamine, N-methylpyrrolidine, DBU, DMAP, N-methylmorpholine, pyridine, methyl pyridine or an inorganic base such as sodium hydroxide, sodium carbonate, sodium bicarbonate, potassium hydroxide, potassium carbonate and potassium bicarbonate. Preferred bases are diisopropylethylamine or N-methylpyrrolidine. The reaction takes place in the presence of suitable solvent to produce the product of formula (I):

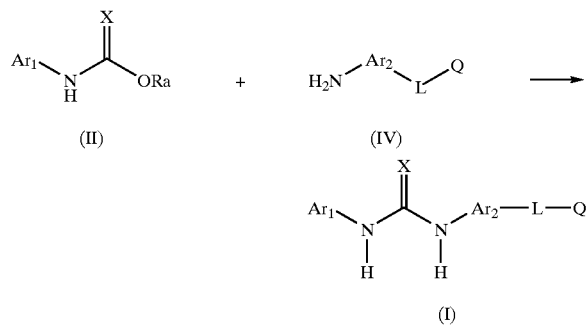

Reaction conditions such as the selection of a suitable solvent, base and temperature can be varied according to the specific compound of the formula(I) that is desired. The reaction can be run in a suitable polar, or a suitable non-polar solvent such as methylene chloride or chloroform or in heptane, hexane, cyclohexane, ethyl acetate, benzene, toluene, xylene, tetrahydropfuran, dioxane, ethyl ether, methyl butyl ether or in a biphasic aqueous/organic mixture. Preferably the solvent will be a polar non-protic organic solvent such as NMP(1-methyl-2-pyrrolidinone), acetonitrile, DMF(N,N-dimethylformamide), DMAC(N,N-dimethylacetamide) or DMSO, more preferably DMSO or NMP, which is heated to an appropriate temperature, preferably about 55–60° C. for about 1.5 hours. Particular separation methods depending on the compound desired will be apparent to those of ordinary skill in the art. A preferred method is shown in Example 1 in the present specification.

A preferred subgeneric aspect of the invention comprises a process of producing compounds of the formula(I) wherein $Ar_2$ is naphthyl, tetrahydronaphthyl, indanyl or indenyl.

A more preferred subgeneric aspect of the invention comprises a process of producing compounds of the formula (I) wherein $Ar_2$ is naphthyl.

A yet more preferred subgeneric aspect of the invention comprises a process of producing compounds of the formula (I), as described in the immediate previous paragraph, wherein:

$Ar_1$ is thiophene or pyrazole;
$Ar_2$ is 1-naphthyl;
L is $C_{1-6}$ saturated or unsaturated branched or unbranched carbon chain wherein
one or more methylene groups are optionally independently replaced by O, N or S; and wherein said linking group is optionally substituted with 0–2 oxo groups and one or more $C_{1-4}$ branched or unbranched alkyl optionally substituted by one or more halogen atoms; or L is cyclopentenyl, cyclohexenyl, cycloheptenyl, each optionally substituted with an oxo group or 1–3 $C_{1-4}$ branched or unbranched alkyl, $C_{1-4}$alkoxy or $C_{1-4}$alkylamino; or L is phenyl, pyridine, furan or thiophene each being optionally independently substituted with 1–3 $C_{1-4}$ branched or unbranched alkyl, $C_{1-4}$alkoxy, hydroxy, cyano, mono- or di-($C_{1-3}$ alkyl)amino, $C_{1-6}$ alkyl-S(O)$_q$ or halogen;

wherein said cyclic group is optionally attached to a $C_{1-4}$ saturated or unsaturated branched or unbranched carbon chain wherein said carbon chain is in turn covalently attached to Q, said carbon chain is optionally partially or fully halogenated and wherein one or more methylene groups are optionally replaced by O, NH, S(O), S(O)$_2$ or S, wherein said methylene groups are further optionally independently substituted with 1–2 oxo groups and one or more $C_{1-4}$ branched or unbranched alkyl optionally substituted by one or more halogen atoms;

$R_1$ is $C_{3-4}$alkyl branched or unbranched, cyclopropyl or cyclohexanyl optionally partially or fully halogenated and optionally substituted with one to three $C_{1-3}$ alkyl groups;

$R_3$ is selected from the group consisting of $C_{1-4}$alkyl branched or unbranched optionally partially or fully halogenated, cyclopentanyl optionally partially or fully halogenated and optionally substituted with one to three $C_{1-3}$ alkyl groups, phenyl, pyridinyl each being optionally substituted with one to five groups selected from the group consisting of a $C_{1-6}$ branched or unbranched alkyl, phenyl, naphthyl, pyridinyl, $C_{1-6}$ branched or unbranched alkyl which is optionally partially or fully halogenated, cyclopropyl, cyclobutyl, cyclopentanyl, cyclohexanyl, cycloheptanyl, bicyclopentanyl, bicyclohexanyl, bicycloheptanyl, phenyl $C_{1-5}$ alkyl, naphthyl $C_{1-5}$ alkyl, halo, hydroxy, cyano, $C_{1-3}$ alkyloxy which may optionally be partially or fully halogenated, phenyloxy, naphthyloxy, pyridinyloxy, nitro, amino, mono- or di-($C_{1-3}$)alkylamino, phenylamino, naphthylamino, pyridinylamino, NH$_2$C(O), a mono- or di-($C_{1-3}$)alkyl aminocarbonyl, $C_{1-5}$ alkyl-C(O)—$C_{1-4}$ alkyl, amino-$C_{1-5}$ alkyl, mono- or di-($C_{1-3}$)alkylamino-$C_{1-5}$ alkyl, amino-S(O)$_2$, di-($C_{1-3}$)alkylamino-S(O)$_2$, $R_4$—$C_{1-5}$ alkyl, $R_5$—$C_{1-5}$ alkoxy, $R_6$—C(O)—$C_{1-5}$ alkyl and $R_7$—$C_{1-5}$ alkyl-N(R$_8$)—; and $R_3$ is alkoxycarbonylalkyl;

A yet further preferred subgeneric aspect of the invention comprises a process of producing compounds of the formula (I), as described in the immediate previous paragraph, wherein $Ar_1$ is pyrazole.

A still yet further preferred subgeneric aspect of the invention comprises a process of producing compounds of the formula (I), as described in the immediate previous paragraph, wherein L is $C_{1-5}$ saturated carbon chain wherein one or more methylene groups are optionally independently replaced by O,N or S; and wherein said linking group is optionally substituted with 0–2 oxo groups and one or more $C_{1-4}$ branched or unbranched alkyl optionally substituted by one or more halogen atoms;

More particularly preferred embodiments of the process of the invention is where L is propoxy, ethoxy, methoxy, methyl, propyl, $C_{3-5}$ acetylene or methylamino each being optionally substituted as described herein and Q is morpholine.

A even more particularly preferred embodiment of L is ethoxy optionally substituted, the base is diisopropylethylamine and the polar non-protic organic solvent is DMSO.

In order that this invention be more fully understood, the following examples are set forth. These examples are for the purpose of illustrating preferred embodiments of this invention, and are not to be construed as limiting the scope of the invention in any way.

SYNTHETIC EXAMPLES

Example 1

1-[3-tert-butyl-1-p-tolyl-1H-pyrazol-5-yl]-3-[4(2-morpholin-4-yl-ethoxy)naphthalen-1-yl]-urea.

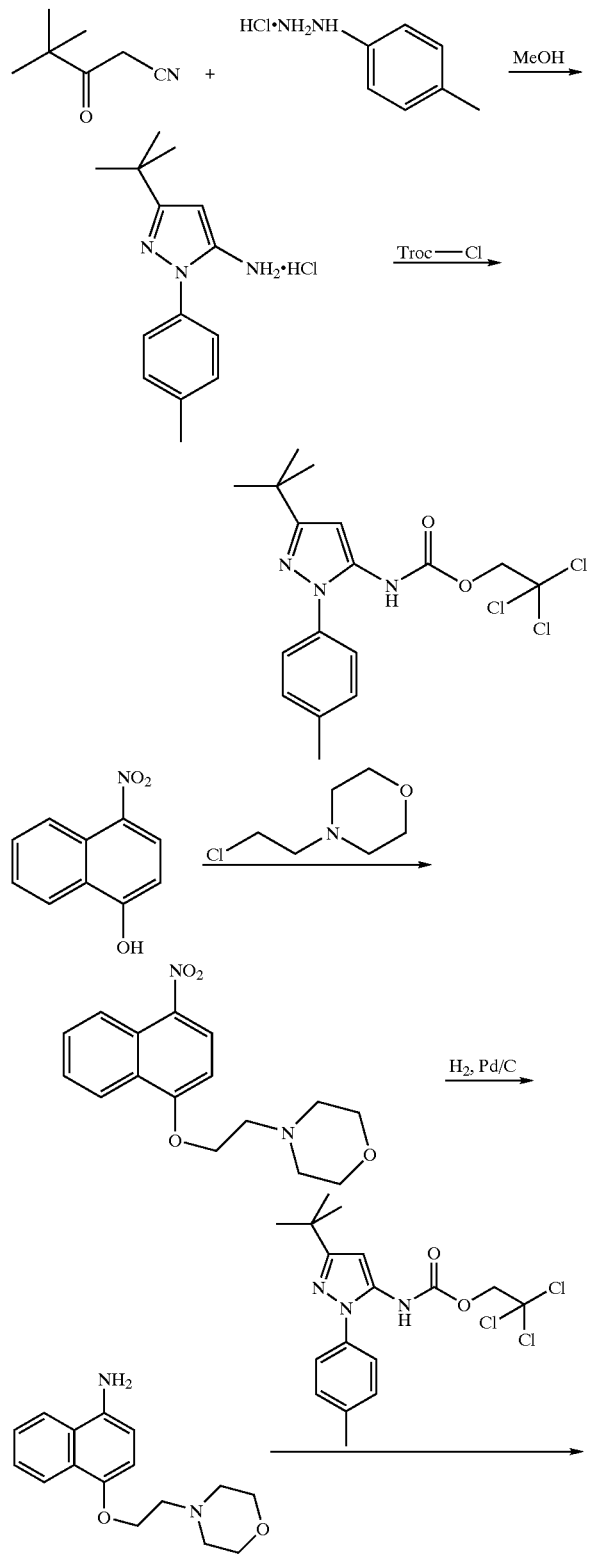

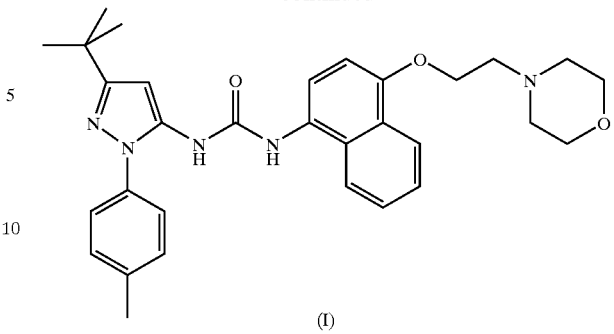

(I)

5-Amino-3-t-butyl-1-p-tolylpyrazole hydrochloride

A solution of pivaloylacetonitrile (750 g, 6.0 mol) and p-tolylhydrazine hydrochloride (660 g, 4.2 mol) in methanol (2.8 L) was refluxed for 3 h. Heptane was added, and methanol was removed by distillation. The product was crystallized from the solution, collected by filtration and dried in vacuum oven to constant weight. Yield: 1.05 kg, 94%. $^1$H NMR δ (CDCl$_3$) 7.50 (d, 2H), 7.30 (d, 2H), 5.60 (s, 1H), 2.45 (s, 3H), 1.40 (s, 9H). MS (CI) m/z 229 (M$^+$+H).

5-(2,2,2-Trichloroethoxycarbonyl)amino-3-t-butyl-1-p-tolylpyrazole

A mixture of 5-amino-3-t-butyl-1-p-tolylpyrazole hydrochloride (300 g, 1.13 mol), water (0.9 L), EtOAc (2.1 L) and NaOH (117 g, 2.84 mol) was stirred between 5–15° C. for 30 min. To this mixture, 2,2,2-trichloroethyl chloroformate (342 g, 1.58 mol) was added over 1 h between 5–15° C. The mixture was stirred at room temperature for 2 h, and then the aqueous layer was separated from the EtOAc layer. The EtOAc layer was washed with brine (2×0.9 L) and dried over MgSO$_4$ (60 g). The EtOAc layer was collected by filtration. To this solution, heptane was added. A part of the solution was removed by distillation. The product was crystallized from the solution, collected by filtration and dried in vacuum oven to constant weight. Yield: 409 g, 90%. $^1$H NMR (CDCl$_3$) δ 7.40 (d, 2H), 7.30 (d, 2H), 6.40 (s, 1H), 4.80 (s, 2H), 2.40 (s, 3H), 1.40 (s, 9H). MS (EI) m/z 404 (M+).

4-Nitro-1-(2-morpholinethoxy)naphthalene

A mixture of 4-nitro-1-hydroxynaphthalene (194 g, 1.0 mol), 4-(2-chloroethyl)morpholine hydrochloride (264 g, 1.4 mol), NaOH (58 g, 1.4 mol), K$_2$CO$_3$ (339 g, 2.4 mol) and 1-methyl-2-pyrrolidinone (1.0 L) was heated to 90–100° C. and held for 1–2 h. The mixture was cooled to 40° C. and water was slowly added. The mixture was cooled to 5° C. and held for 4 h. The product was collected by filtration, washed with water, cyclohexane and dried in vacuum to constant weight. Yield: 227 g, 75%. $^1$H NMR (CDCl$_3$) δ 8.76 (d, 1H), 8.38 (m, 2H), 7.74 (dd, 1H), 7.58 (dd, 1 H), 6.79 (d, 1 H), 4.38 (dd, 2 H), 3.74 (d, 4 H), 2.98 (dd, 2H), 2.65 (d, 4 H). MS (EI) m/z 303 (M+1).

4-Amino-1-(2-morpholinethoxy)naphthalene hydrochloride

A mixture of 4-nitro-1-(2-morpholinethoxy)naphthalene (40 g, 0.13 mol), MeOH (280 mL) and Pd/C (50% water, 1.2 g) was hydrogenated under 30 psi for 24 h. The catalyst was filtered through a layer of diatomaceous earth under nitrogen. To this filtrate 20 mL of HCl (37%) and cyclohexane (200 mL) were added. The solvent was removed under reduced pressure and the product collected by filtration. The product was dried in vacuum to constant weight. Yield: 33 g, 82%. $^1$H NMR (DMSO) δ 8.38 (d, 1H), 8.00 (d, 1H), 7.72 (dd, 1H), 7.64 (m, 2H), 7.05 (d, 1H), 4.62 (s, 2H), 4.00 (b, 4H), 3.88 (s, 2H), 3.40 (b, 4H). MS (EI) m/z 273 (M+).

1-[3-tert-butyl-1-p-tolyl-1H-pyrazol-5-yl]-3-[4-(2-morpholin-4-yl-ethoxy)naphthalen-1-yl]-urea A solution of 5-(2,2,2-trichloroethoxycarbonyl)amino-3-t-butyl-1-p-tolylpyrazole (10.6 g, 26 mmol), 4-amino-1-(2-morpholinethoxy)naphthalene (free base from HCl salt above, 7.16 g, 26 mmol), diisopropylethylamine (3.2 g, 25 mmol) and DMSO (75 mL) was heated to 55–60° C. and held for 1.5 h. To this solution, ethyl acetate (100 mL) was added. The organic layer was washed with brine (4×50 mL), and dried over MgSO$_4$. The solvent was removed under reduced pressure, and residue was crystallized from acetonitrile (50 mL) at 0° C. The product was collected by filtration, recrystallized from isopropanol and dried in vacuum to constant weight, m.p.: 151–152° C. Yield: 11.4 g, 87%. $^1$H NMR (DMSO) δ8.75 (s, 1H), 8.51 (s, 1H), 8.21 (d, 1H), 7.85 (d, 1H), 7.65 (d, 1H), 7.55 (m, 2H), 7.49 (dd, 1H), 7.35 (dd, 1H), 6.95 (d, 1H), 6.38 (s, 1H), 4.26 (dd, 2H), 3.60 (dd, 4H), 2.81 (dd, 2H), 2.55 (dd, 4H), 2.38 (s, 3H), 1.29 (s, 9H). MS (CI) m/z 528 (M++1).

The following additional non-limiting examples can be made using the novel process of the invention:

Example 2

1-[3-tert-butyl-1-p-tolyl-1H-pyrazol-5-yl]-3-{4-[5-(morpholin-4-ylmethyl)fur-2-yl]naphthalen-1-yl} urea

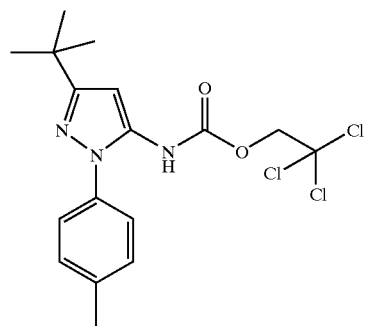

+

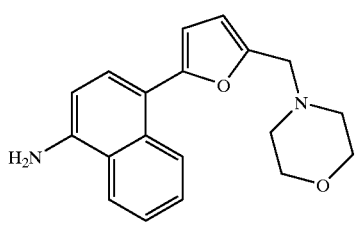

→

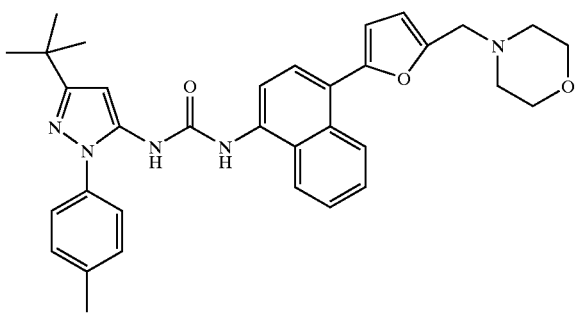

A solution of 5-(2,2,2-trichloroethoxycarbonyl)amino-3-t-butyl-1-p-tolylpyrazole (26 mmol), 1-amino-4-[5-(morpholin-4-ylmethyl)fur-2-yl]naphthalene (26 mmol), diisopropylethylamine (25 mmol) and DMSO (75 mL) is heated to 55–90° C. and held for 2–8 h. To this solution, ethyl acetate (100 mL) is added. The organic layer is washed with brine (4×50 mL), and dried over MgSO$_4$. The solvent is removed under reduced pressure, and residue is crystallized from a suitable solvent such as acetonitrile (50 mL) at 0° C. The product is collected by filtration and recrystallized from a suitable solvent such as isopropanol and dried in vacuum to constant weight.

Example 3

1-[3-tert-butyl-1-p-tolyl-1H-pyrazol-5-yl]-3-{4-[6-(morpholin-4-ylmethyl)pyridin-3-yl]naphthalen-1-yl} urea

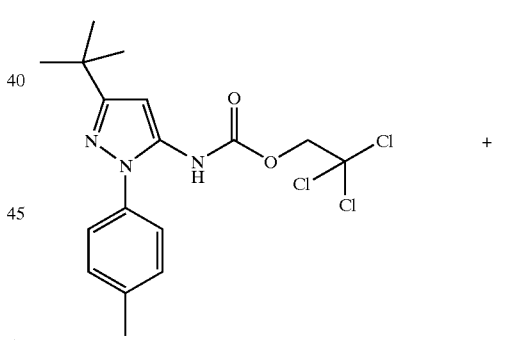

+

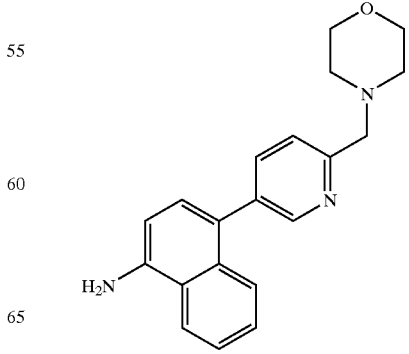

→

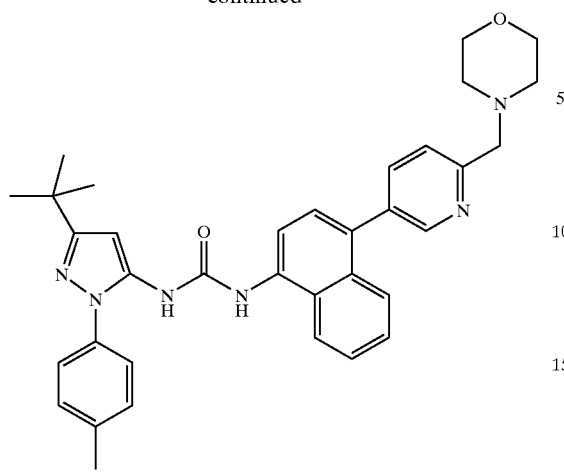
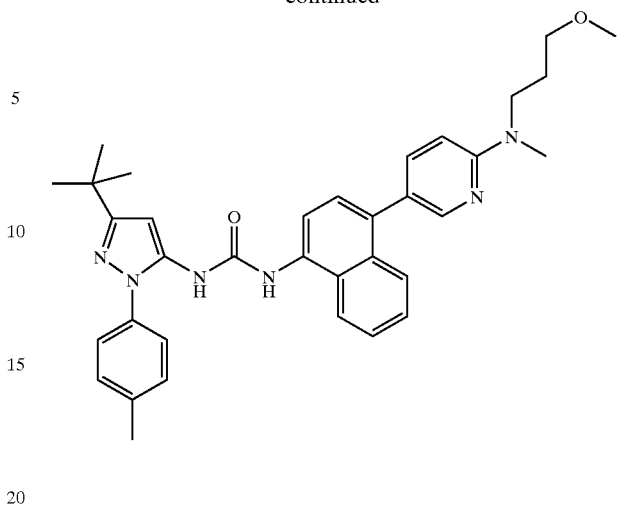

A solution of 5-(2,2,2-trichloroethoxycarbonyl)amino-3-t-butyl-1-p-tolylpyrazole (26 mmol), 1-amino-4-[6-(morpholin-4-ylmethyl)pyridin-3-yl]naphthalene (26 mmol), diisopropylethylamine (25 mmol) and DMSO (75 mL) is heated to 55–90° C. and held for 2–8 h. To this solution, ethyl acetate (100 mL) is added. The organic layer is washed with brine (4×50 mL), and dried over MgSO₄. The solvent is removed under reduced pressure, and residue is crystallized from a suitable solvent such as acetonitrile (50 mL) at 0° C. The product is collected by filtration and recrystallized from a suitable solvent such as isopropanol and dried in vacuum to constant weight.

A solution of 5-(2,2,2-trichloroethoxycarbonyl)amino-3-t-butyl-1-p-tolylpyrazole (26 mmol), 1-amino-4-{6-[(3-methoxypropyl)methylamino]pyridin-3-yl}naphthalene (26 mmol), diisopropylethylamine (25 mmol) and DMSO (75 mL) is heated to 55–90° C. and held for 2–8 h. To this solution, ethyl acetate (100 mL) is added. The organic layer is washed with brine (4×50 mL), and dried over MgSO₄. The solvent is removed under reduced pressure, and residue is crystallized from a suitable solvent such as acetonitrile (50 mL) at 0° C. The product is collected by filtration and recrystallized from a suitable solvent such as isopropanol and dried in vacuum to constant weight.

Example 4

1-[3-tert-butyl-1-p-tolyl-1H-pyrazol-5-yl]-3-(4-{6-[(3-methoxypropyl)methylamino]pyridin-3-yl}naphthalen-1-yl)urea Example 5

1-[3-tert-butyl-1-p-tolyl-1H-pyrazol-5-yl]-3-[4-(3-pyridin-4-yl-propoxy)naphthalen-1-yl]-urea

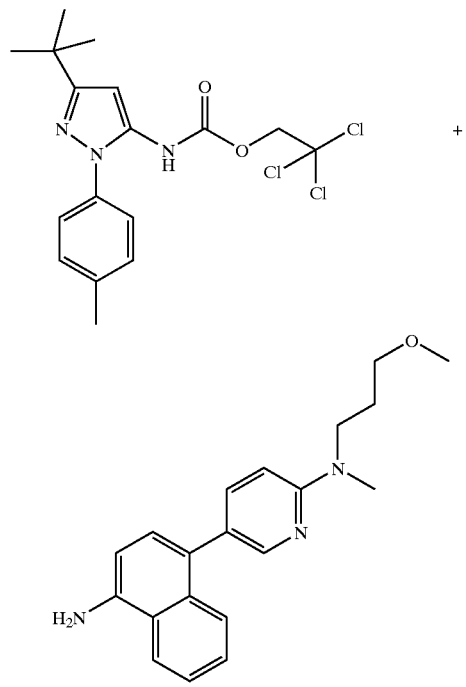
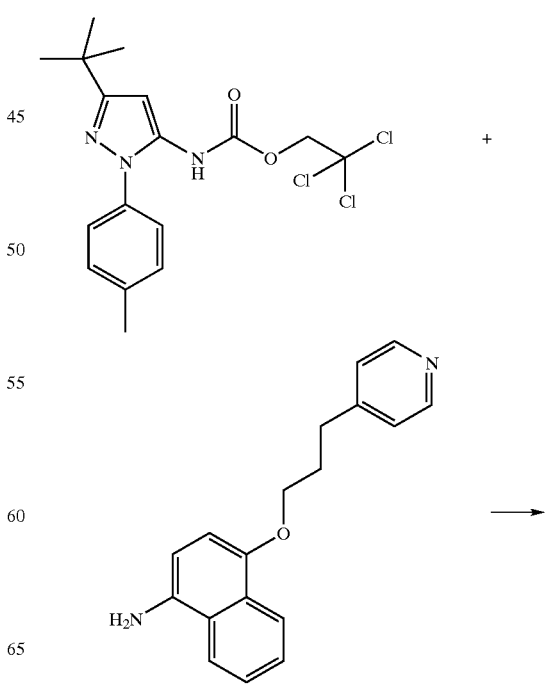

17
-continued

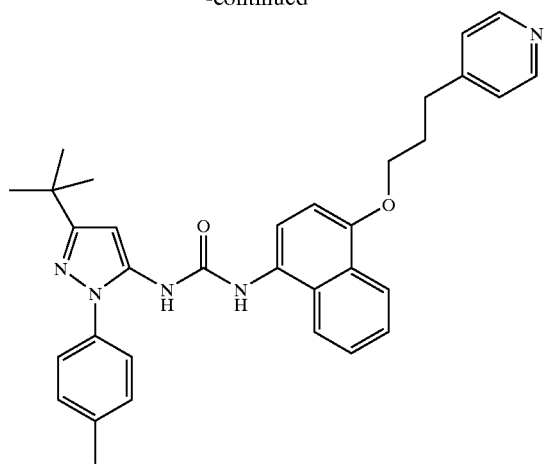

A solution of 5-(2,2,2-trichloroethoxycarbonyl)amino-3-t-butyl-1-p-tolylpyrazole (26 mmol), 1-amino-4-(3-pyridin-4-ylpropoxy)naphthalene (26 mmol), diisopropylethylamine (25 mmol) and DMSO (75 mL) is heated to 55–90° C. and held for 2–8 h. To this solution, ethyl acetate (100 mL) is added. The organic layer is washed with brine (4×50 mL), and dried over MgSO$_4$. The solvent is removed under reduced pressure, and residue is crystallized from a suitable solvent such as acetonitrile (50 mL) at 0° C. The product is collected by filtration and recrystallized from a suitable solvent such as isopropanol and dried in vacuum to constant weight.

Example 6

1-[3-tert-butyl-1-(2-methylpyridin-5-yl)-1H-pyrazol-5-yl]-3-[4-(pyridin-4-4-yl-methoxy)naphthalen-1-yl]-urea 18
-continued

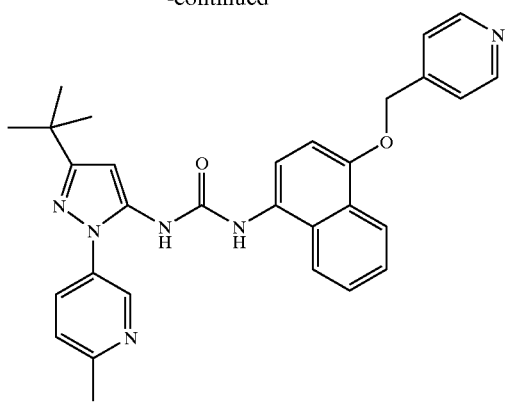

A solution of 5-(2,2,2-trichloroethoxycarbonyl)amino-3-t-butyl-1-(2-methylpyridin-5-yl)pyrazole (26 mmol), 1-amino-4-(pyridin-4-ylmethoxy)naphthalene (26 mmol), diisopropylethylamine (25 mmol) and DMSO (75 mL) is heated to 55–90° C. and held for 2–8 h. To this solution, ethyl acetate (100 mL) is added. The organic layer is washed with brine (4×50 mL), and dried over MgSO$_4$. The solvent is removed under reduced pressure, and residue is crystallized from a suitable solvent such as acetonitrile (50 mL) at 0° C. The product is collected by filtration and recrystallized from a suitable solvent such as isopropanol and dried in vacuum to constant weight.

Example 7

1-[3-tert-butyl-1-p-tolyl-1H-pyrazol-5-yl]-3-[4-(2-pyridin-4-yl-ethenyl)naphthalen-1-yl]-urea

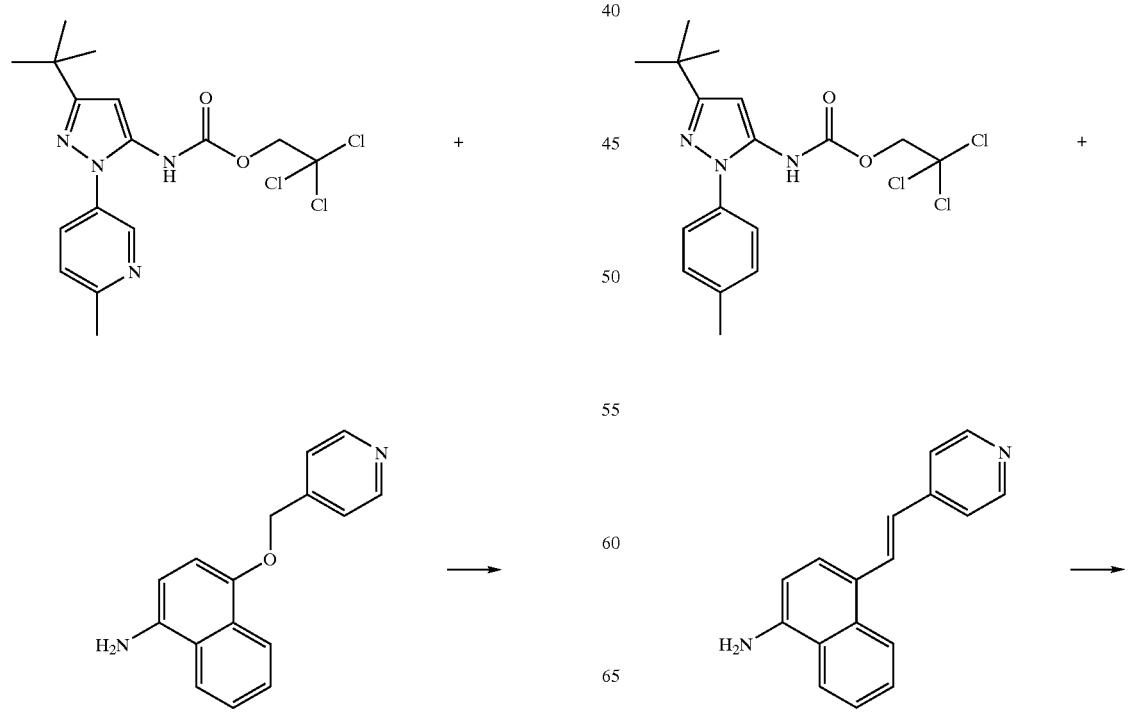

19
-continued

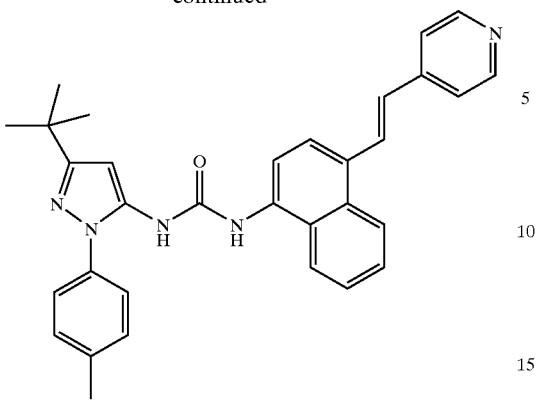

A solution of 5-(2,2,2-trichloroethoxycarbonyl)amino-3-t-butyl-1-p-tolylpyrazole (26 mmol), 1-amino-4-(2-pyridin-4-yl-ethenyl)naphthalene (26 mmol), diisopropylethylamine (3.2 g, 25 mmol) and DMSO (75 mL) is heated to 55–90° C. and held for 2–8 h. To this solution, ethyl acetate (100 mL) is added. The organic layer is washed with brine (4×50 mL), and dried over MgSO$_4$. The solvent is removed under reduced pressure, and residue is crystallized from a suitable solvent such as acetonitrile (50 mL) at 0° C. The product is collected by filtration and recrystallized from a suitable solvent such as isopropanol and dried in vacuum to constant weight.

Example 8

1-(5-tert-Butyl-2-methyphenyl)-3-[4-(6-morpholin-4-ylmethyl-pyridin-3-yl)-naphthalen-1-yl]urea

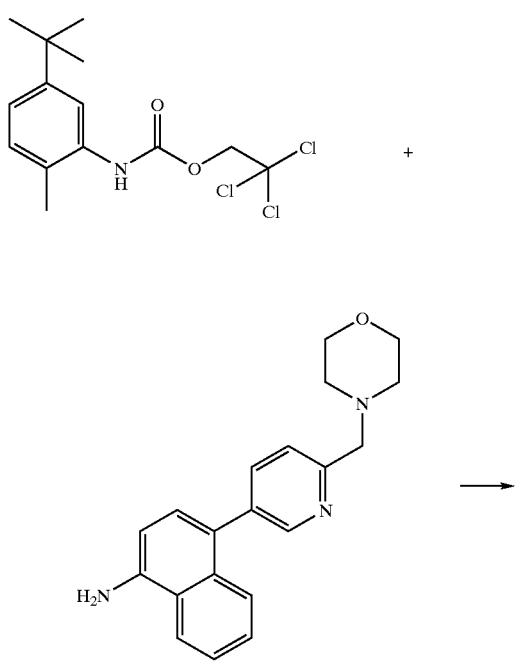

20
-continued

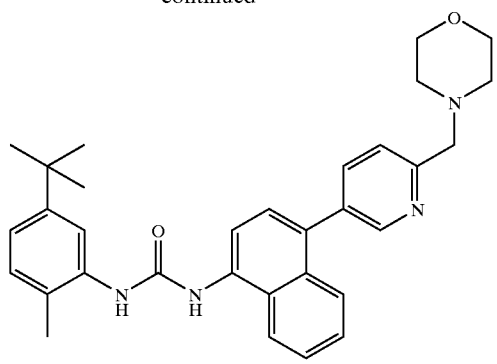

A solution of 5-t-butyl-2-methyl-1-(2,2,2-trichloroethoxycarbonyl)aminobenzene (26 mmol), 1-amino-4-[6-(morpholin-4-ylmethyl)pyridin-3-yl]naphthalene (26 mmol), diisopropylethylamine (3.2 g, 25 mmol) and DMSO (75 mL) is heated to 55–60° C. and held for 1.5 h. To this solution, ethyl acetate (100 mL) is added. The organic layer is washed with brine (4×50 mL), and dried over MgSO$_4$. The solvent is removed under reduced pressure, and residue is crystallized from a suitable solvent such as acetonitrile (50 mL) at 0° C. The product is collected by filtration and recrystallized from a suitable solvent such as isopropanol and dried in vacuum to constant weight.

What is claimed is:

1. A process of producing an intermediate compound of formula (IV):

(IV)

comprising:
  reducing compound of formula (III) by catalytic hydrogenation with a Pd/C catalyst under about 30 psi for about 1–24 hours:

(III)

wherein:
  Z is a nitro or nitroso group;
  Ar$_2$ is phenyl, naphthyl, quinoline, isoquinoline, tetrahydronaphthyl, tetrahydroquinoline, tetrahydroisoquinoline, benzimidazole, benzofuran, indanyl, indenyl or indole each being optionally substituted with one to three R$_2$ groups;
  R$_2$ is selected from the group consisting of:
    a C$_{1-6}$ branched or unbranched alkyl optionally partially or fully halogenated, acetyl, aroyl, C$_{1-4}$ branched or unbranched alkoxy optionally partially or fully halogenated, halogen, methoxycarbonyl and phenylsulfonyl;
  L, a linking group, is:
    C$_{1-10}$ saturated or unsaturated branched or unbranched carbon chain;
      wherein one or more methylene groups are optionally independently replaced by O, NH or S; and
      wherein said linking group is optionally substituted with oxo and one or more C$_{1-4}$ branched or unbranched alkyl optionally substituted by one or more halogen atoms;

or L is a cyclic group which is:

a) a $C_{5-8}$ cycloalkyl or cycloalkenyl optionally substituted with 1–2 oxo groups, 1–3 $C_{1-4}$ branched or unbranched alkyl, $C_{1-4}$ alkoxy or $C_{1-4}$ alkylamino chains;

b) phenyl, furan, thiophene, pyrrole, imidazolyl, pyridine, pyrimidine, pyridinone, dihydropyridinone, maleimide, dihydromaleimide, piperidine, piperazine or pyrazine each being optionally independently substituted with 1–3 $C_{1-4}$ branched or unbranched alkyl, $C_{1-4}$alkoxy, hydroxy, cyano, mono- or di-($C_{1-3}$ alkyl)amino, $C_{1-6}$ alkyl-S(O)$_q$, or halogen;

wherein said cyclic group is optionally attached to a $C_{1-4}$ saturated or unsaturated branched or unbranched carbon chain wherein said carbon chain is in turn covalently attached to Q, said carbon chain is optionally partially or fully halogenated and wherein one or more methylene groups are optionally replaced by O, NH, S(O), S(O)$_2$ or S, wherein said methylene groups are further optionally independently substituted with oxo and one or more $C_{1-4}$ branched or unbranched alkyl optionally substituted by one or more halogen atoms;

Q is optionally substituted with one to three groups selected from the group consisting of $C_{1-6}$ alkyl, $C_{1-6}$ alkoxy, hydroxy, mono- or di-($C_{1-3}$ alkyl)amino-$C_{1-3}$ alkyl, phenylamino-$C_{1-3}$ alkyl and $C_{1-3}$ alkoxy-$C_{1-3}$ alkyl;

to produce the intermediate of formula (IV).

2. The process according to claim 1 wherein:

Ar$_2$ is naphthyl, tetrahydronaphthyl, indanyl or indenyl.

3. The process according to claim 2 wherein Ar$_2$ is naphthyl.

4. The process according to claim 3 wherein

Ar$_2$ is 1-naphthyl;

L is $C_{1-6}$ saturated or unsaturated branched or unbranched carbon chain wherein one or more methylene groups are optionally independently replaced by O, NH or S; and wherein said linking group is optionally substituted with oxo and one or more $C_{1-4}$ branched or unbranched alkyl optionally substituted by one or more halogen atoms;

or L is cyclopentenyl, cyclohexenyl, cycloheptenyl, each optionally substituted with an oxo group or 1–3 $C_{1-4}$ branched or unbranched alkyl, $C_{1-4}$alkoxy or $C_{1-4}$alkylamino; or L is phenyl, pyridine, furan or thiophene each being optionally independently substituted with 1–3 $C_{1-4}$ branched or unbranched alkyl, $C_{1-4}$alkoxy, hydroxy, cyano, mono- or di-($C_{1-3}$ alkyl)amino, $C_{1-6}$ alkyl-S(O)$_q$ or halogen;

wherein said cyclic group is optionally attached to a $C_{1-4}$ saturated or unsaturated branched or unbranched carbon chain wherein said carbon chain is in turn covalently attached to Q, said carbon chain is optionally partially or fully halogenated and wherein one or more methylene groups are optionally replaced by O, NH, S(O), S(O)$_2$ or S, wherein said methylene groups are further optionally independently substituted with oxo and one or more $C_{1-4}$ branched or unbranched alkyl optionally substituted by one or more halogen atoms.

5. The process according to claim 4 wherein

L is $C_{1-5}$ saturated carbon chain wherein one or more methylene groups are optionally independently replaced by O, NH or S; and wherein said linking group is optionally substituted with oxo and one or more $C_{1-4}$ branched or unbranched alkyl optionally substituted by one or more halogen atoms.

6. The process according to claim 5 wherein:

L is propyleneoxy, ethyleneoxy, methyleneoxy, methylene, propylene, $C_{3-5}$ acetylene or methylamino and Q is morpholine.

7. The process according to claim 6 wherein L is ethyleneoxy.

* * * * *

UNITED STATES PATENT AND TRADEMARK OFFICE
CERTIFICATE OF CORRECTION

PATENT NO. : 6,835,832 B2
DATED : December 28, 2004
INVENTOR(S) : Lin-Hua Zhang and Lei Zhu It is certified that error appears in the above-identified patent and that said Letters Patent is hereby corrected as shown below:

Column 21,
Line 26, reads "Q is optionally substituted with one to three groups…"
should read:
-- Q is morpholine optionally substituted with one to three groups --

Signed and Sealed this

Twelfth Day of April, 2005

JON W. DUDAS
*Director of the United States Patent and Trademark Office*